(12) United States Patent
Zhu et al.

(10) Patent No.: US 8,825,172 B2
(45) Date of Patent: Sep. 2, 2014

(54) TECHNIQUES FOR ELECTRONICALLY ASSESSING ELECTRODE CONDITION AND PERI-ELECTRODE TISSUE CONDUCTIVITY CHANGE PRE- AND POST-MRI

(71) Applicant: Boston Scientific Neuromodulation Corporation, Valencia, CA (US)

(72) Inventors: Changfang Zhu, Valencia, CA (US); Kerry Bradley, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/944,593

(22) Filed: Jul. 17, 2013

(65) Prior Publication Data

US 2014/0031901 A1    Jan. 30, 2014

Related U.S. Application Data

(60) Provisional application No. 61/676,807, filed on Jul. 27, 2012.

(51) Int. Cl.
| | |
|---|---|
| *A61N 1/08* | (2006.01) |
| *A61N 1/36* | (2006.01) |
| *A61B 5/055* | (2006.01) |
| *A61B 5/053* | (2006.01) |

(52) U.S. Cl.
CPC ............... *A61N 1/36125* (2013.01); *A61N 1/08* (2013.01); *A61N 2001/083* (2013.01); *A61B 5/055* (2013.01); *A61N 2001/086* (2013.01); *A61B 5/053* (2013.01); *A61N 1/36128* (2013.01)
USPC .......................................................... 607/60

(58) Field of Classification Search
CPC ............ A61N 1/3718; A61N 1/37258; A61N 2001/086; A61N 1/37; A61N 1/372; A61N 1/37247; A61N 1/37264; A61N 1/37282; A61N 1/3925; A61N 2001/083; A61N 1/37252; A61N 1/37223; A61N 1/08; A61N 1/36125; A61N 1/36128; A61B 5/055; A61B 5/053; G01R 33/288; G06F 19/3412
USPC ....................................................... 607/60–63
See application file for complete search history.

(56) References Cited

U.S. PATENT DOCUMENTS

| | | |
|---|---|---|
| 6,516,227 B1 | 2/2003 | Meadows et al. |
| 6,895,280 B2 | 5/2005 | Meadows et al. |

(Continued)

OTHER PUBLICATIONS

U.S. Appl. No. 61/612,241, Neurostimulation System for Preventing Magnetically Induced Currents in Electronic Circuitry, Inventor: Kiran Gururaj, et al., filed Mar. 16, 2012.

(Continued)

*Primary Examiner* — Rex R Holmes
(74) *Attorney, Agent, or Firm* — Vista IP Law Group LLP

(57) ABSTRACT

A neurostimulation system and method of operating an implantable neurostimulation device configured for outputting electrical stimulation energy to at least one electrode in accordance with a set of stimulation parameters. The implantable neurostimulation device may be switched from a normal operating mode to a Magnetic Resonance Imaging (MRI) operating mode. Electrical parameter measurements may be repeatedly acquired at each of the electrode(s) in response to the placement of the implantable stimulation system in the MRI mode. A corrective action may be performed based on at least one of the repeatedly acquired electrical parameter measurements.

18 Claims, 6 Drawing Sheets

(56) References Cited

U.S. PATENT DOCUMENTS

| | | |
|---|---|---|
| 6,993,384 B2 | 1/2006 | Bradley et al. |
| 7,239,920 B1 | 7/2007 | Thacker et al. |
| 7,317,948 B1 | 1/2008 | King et al. |
| 7,539,538 B2 | 5/2009 | Parramon et al. |
| 7,650,184 B2 | 1/2010 | Walter |
| 8,019,439 B2 | 9/2011 | Kuzma et al. |
| 8,131,357 B2 | 3/2012 | Bradley et al. |
| 2003/0139781 A1 | 7/2003 | Bradley et al. |
| 2005/0267546 A1 | 12/2005 | Parramon et al. |
| 2006/0224222 A1 | 10/2006 | Bradley et al. |
| 2007/0168004 A1 | 7/2007 | Walter |
| 2007/0168007 A1 | 7/2007 | Kuzma et al. |
| 2007/0208394 A1 | 9/2007 | King et al. |
| 2009/0157155 A1 | 6/2009 | Bradley |
| 2011/0160808 A1* | 6/2011 | Lyden et al. .................... 607/63 |
| 2011/0257509 A1 | 10/2011 | Olsen et al. |
| 2012/0101537 A1 | 4/2012 | Peterson et al. |
| 2012/0109001 A1 | 5/2012 | Ellingson |

OTHER PUBLICATIONS

U.S. Appl. No. 61/664,061, Neurostimulation System for Enabling Magnetic Field Sensing with a Shut-Down Hall Sensor, Inventor: Emanuel Feldman, et al., filed Jun. 25, 2012.

PCT International Search Report for PCT/US2013/050916, Applicant: Boston Scientific Neuromodulation Corporation, Form PCT/ISA/210 and 220, dated Nov. 5, 2013 (5pages).

PCT Written Opinion of the International Search Authority for PCT/US2013/050916, Applicant: Boston Scientific Neuromodulation Corporation, Form PCT/ISA/237, dated Nov. 5, 2013 (6pages).

* cited by examiner

TECHNIQUES FOR ELECTRONICALLY ASSESSING ELECTRODE CONDITION AND PERI-ELECTRODE TISSUE CONDUCTIVITY CHANGE PRE- AND POST-MRI

RELATED APPLICATION DATA

The present application claims the benefit under 35 U.S.C. §119 to U.S. provisional patent application Ser. No. 61/676,807, filed Jul. 27, 2012. The foregoing application is hereby incorporated by reference into the present application in its entirety.

FIELD OF THE INVENTION

The present invention relates to tissue stimulation systems, and in particular, MRI-compatible neurostimulators.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., Arrhythmias). Spinal Cord Stimulation (SCS) systems have long been accepted as a therapeutic modality for the treatment of chronic pain syndromes, and the application of tissue stimulation has begun to expand to additional applications such as Angina Pectoralis and Incontinence. Deep Brain Stimulation (DBS) has also been applied therapeutically for well over a decade for the treatment of refractory chronic pain syndromes, and DBS has also recently been applied in additional areas such as movement disorders and Epilepsy. Further, in recent investigations Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems such as the Freehand system by NeuroControl (Cleveland, Ohio) have been applied to restore some functionality to paralyzed extremities in spinal cord injury patients.

Each of these implantable neurostimulation systems typically includes at least one stimulation lead implanted at the desired stimulation site and an Implantable Pulse Generator (IPG) implanted remotely from the stimulation site, but coupled either directly to the stimulation lead(s) or indirectly to the stimulation lead(s) via one or more lead extensions. Thus, electrical pulses can be delivered from the neurostimulator to the electrodes carried by the stimulation lead(s) to stimulate or activate a volume of tissue in accordance with a set of stimulation parameters and provide the desired efficacious therapy to the patient.

The neurostimulation system may further comprise a handheld Remote Control (RC) to remotely instruct the neurostimulator to generate electrical stimulation pulses in accordance with selected stimulation parameters. The RC may, itself, be programmed by a technician attending the patient, for example, by using a Clinician's Programmer (CP), which typically includes a general purpose computer, such as a laptop, with a programming software package installed thereon.

IPGs are routinely implanted in patients who are in need of Magnetic Resonance Imaging (MRI). Thus, when designing implantable neurostimulation systems, consideration must be given to the possibility that the patient in which neurostimulator is implanted may be subjected to electro-magnetic forces generated by MRI scanners, which may potentially cause damage to the neurostimulator as well as discomfort to the patient.

In particular, in MRI, spatial encoding relies on successively applying magnetic field gradients. The magnetic field strength is a function of position and time with the application of gradient fields throughout the imaging process. Gradient fields typically switch gradient coils (or magnets) ON and OFF thousands of times in the acquisition of a single image in the presence of a large static magnetic field. Present-day MRI scanners can have maximum gradient strengths of 100 mT/m and much faster switching times (slew rates) of 150 mT/m/ms, which is comparable to stimulation therapy frequencies. Typical MRI scanners create gradient fields in the range of 100 Hz to 30 KHz, and Radio Frequency (RF) fields of 64 MHz for a 1.5 Tesla scanner and 128 MHz for a 3 Tesla scanner.

In an MRI environment, the radiated RF fields may impinge on an IPG and cause different types of problems. For example, MRI-induced heating via the stimulation lead(s) is a risk incurred by patients implanted with IPGs. While the mechanism and degree of heating is a complicated issue, it has clearly been demonstrated in tissue phantoms that electrodes with faulty connections or compromised insulation may tend to exacerbate the heating problem. This problem is made more challenging if the faulty connections are intermittent, such that an electrode integrity check performed prior to the MRI may not indicate a defective electrode that may otherwise be temporarily compromised during the MRI (say due to a slight postural shift while the patient is undergoing the MRI). Therefore, even though IPGs may be designed to be MRI-compatible or the MRI procedure is well-controlled to limit the heat generation, patients may still be exposed to risk if the stimulation lead integrity breaks down. In addition, MRI safety studies for neurostimulation systems, such as cardiac pacemakers, have demonstrated that the electrode-tissue coupling efficiency can change from a pre-MRI procedure to a post-MRI procedure.

There, thus, remains a need to minimize tissue damage or discomfort of the patient due to heating of faulty stimulation leads during an MRI procedure, as well as ensuring that effective stimulation is provided to the patient during or after an MRI procedure.

SUMMARY OF THE INVENTION

In accordance with a first aspect of the present inventions, a neurostimulation system comprises at least one stimulation lead carrying at least one electrode, and stimulation output circuitry coupled to the at least one stimulation lead. The stimulation output circuitry is configured for outputting electrical stimulation energy to the at least one electrode in accordance with a set of stimulation parameters.

The neurostimulation system further comprises a controller/processor configured for placing the implantable stimulation system between a Magnetic Resonance Imaging (MRI) operating mode and a normal operating mode. In one embodiment, the neurostimulation system further comprises a user interface configured for receiving input from a user, in which case, the controller/processor may be configured for placing the implantable stimulation system in the MRI operating mode in response to the user input. In another embodiment, the monitoring circuitry is configured for sensing energy emitted by an MRI scanner, in which case, the controller/processor may be configured for placing the implantable stimulation system in the MRI operating mode in response to the sensed energy.

The neurostimulation system further comprises monitoring circuitry configured for repeatedly acquiring electrical parameter measurements (e.g., one of an impedance measurement and a field potential measurement) at each of the electrode(s) in response to the placement of the implantable stimulation system in the MRI mode. In one embodiment, the controller/processor is configured for instructing the stimulation output circuitry to convey electrical energy to each of the electrode(s), and each of the electrical parameter measurements is taken by measuring at least one electrical parameter in response to the conveyed electrical energy.

The controller/processor is further configured for performing a corrective action based on at least one of the repeatedly acquired electrical parameter measurements. In one embodiment, the controller/processor is configured for determining a defect (e.g., a short circuit or an open circuit) in at least one of the electrodes based on the electrical parameter measurement (s), in which case, the corrective action comprises generating an alert signal (e.g., a binary signal, such as a visual signal, an aural signal, a vibratory signal, and a modulated neurostimulation signal) in response to determining the defect. In another embodiment, the controller/processor is configured for determining an electrode-tissue coupling efficiency based on the electrical parameter measurement(s), and comparing the determined electrode-tissue coupling efficiency to a reference electrode-tissue coupling efficiency, in which case, the corrective action may comprise generating a new set of stimulation parameters based on the comparison. The stimulation output circuitry may be configured for outputting electrical stimulation energy to the electrode(s) in accordance with the new set of stimulation parameters.

In accordance with a second aspect of the present inventions, a method of operating an implantable neurostimulation device configured for outputting electrical stimulation energy to at least one electrode in accordance with a set of stimulation parameters is provided. The method comprises switching the implantable neurostimulation device from a normal operating mode to a Magnetic Resonance Imaging (MRI) operating mode. One method further comprises receiving input from a user, in which case, the neurostimulation device may be switched to the MRI operating mode in response to the user input. Another method further comprises sensing energy emitted by an MRI scanner, in which case, the implantable neurostimulation device may be switched to the MRI operating mode in response to the sensed energy.

The method further comprises repeatedly acquiring electrical parameter measurements (e.g., one of an impedance measurement and a field potential measurement) at each of the electrode(s) in response to the placement of the implantable stimulation system in the MRI mode. In one method, the electrical energy is conveyed to each of the electrode(s), and each of the electrical parameter measurements is taken by measuring at least one electrical parameter in response to the conveyed electrical energy.

The method further comprises performing a corrective action based on at least one of the repeatedly acquired electrical parameter measurements. One method further comprises determining a defect in at least one of the electrodes based on electrical parameter measurement(s), in which case, the corrective action may comprise generating an alert signal (e.g., a binary signal, such as a visual signal, an aural signal, a vibratory signal, and a modulated neurostimulation signal) in response to determining the defect. Another method further comprises determining an electrode-tissue coupling efficiency based on the electrical parameter measurement(s), and comparing the determined electrode-tissue coupling efficiency to a reference electrode-tissue coupling efficiency, in which case, the corrective action may comprise generating a new set of stimulation parameters based on the comparison. The method may further comprise outputting electrical stimulation energy to the electrode(s) in accordance with the new set of stimulation parameters.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that while the invention lends itself well to applications in SCS, the invention, in its broadest aspects, may not be so limited. Rather, the invention may be used with any type of implantable electrical circuitry used to stimulate tissue. For example, the present invention may be used as part of a multi-lead system such as a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
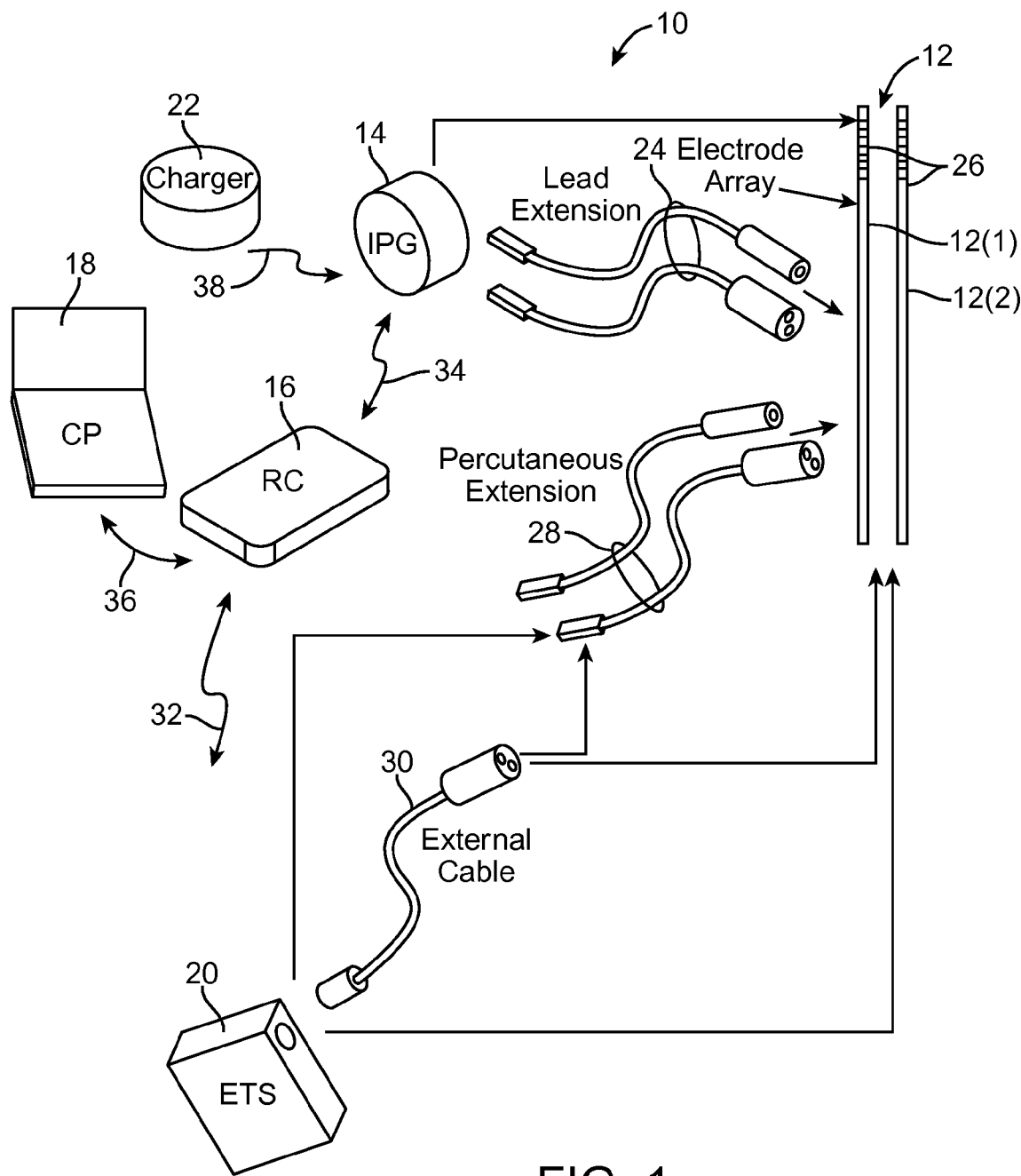
FIG. 1 is plan view of one embodiment of an SCS system arranged in accordance with the present inventions.

Turning first to FIG. 1, an exemplary SCS system 10 generally comprises a plurality of percutaneous neurostimulation leads 12 (in this case, two percutaneous leads 12(1) and 12(2)), an implantable pulse generator (IPG) 14, an external remote control (RC) 16, a Clinician's Programmer (CP) 18, an External Trial Stimulator (ETS) 20, and an external charger 22.

The IPG 14 is physically connected via one or more percutaneous lead extensions 24 to the neurostimulation leads 12, which carry a plurality of electrodes 26 arranged in an array. In the illustrated embodiment, the neurostimulation leads 12 are percutaneous leads, and to this end, the electrodes 26 are arranged in-line along the neurostimulation leads 12. Alternatively, a surgical paddle lead can be used in place of or in addition to the percutaneous leads. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the neurostimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and stimulation lead 12 is implanted, the RC 16 may be used to telemetrically control the IPG 14 via a bi-directional RF communications link 34. Such control allows the IPG 14 to be turned on or off and to be programmed with different stimulation programs after implantation. Once the IPG 14 has been programmed, and its power source has been charged or otherwise replenished, the IPG 14 may function as programmed without the RC 16 being present.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown).

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For purposes of brevity, the details of the CP 18, ETS 20, and external charger 22 will not be described herein. Details of exemplary embodiments of these devices are disclosed in U.S. Pat. No. 6,895,280, which has been previously incorporated herein by reference.

Figure 2:
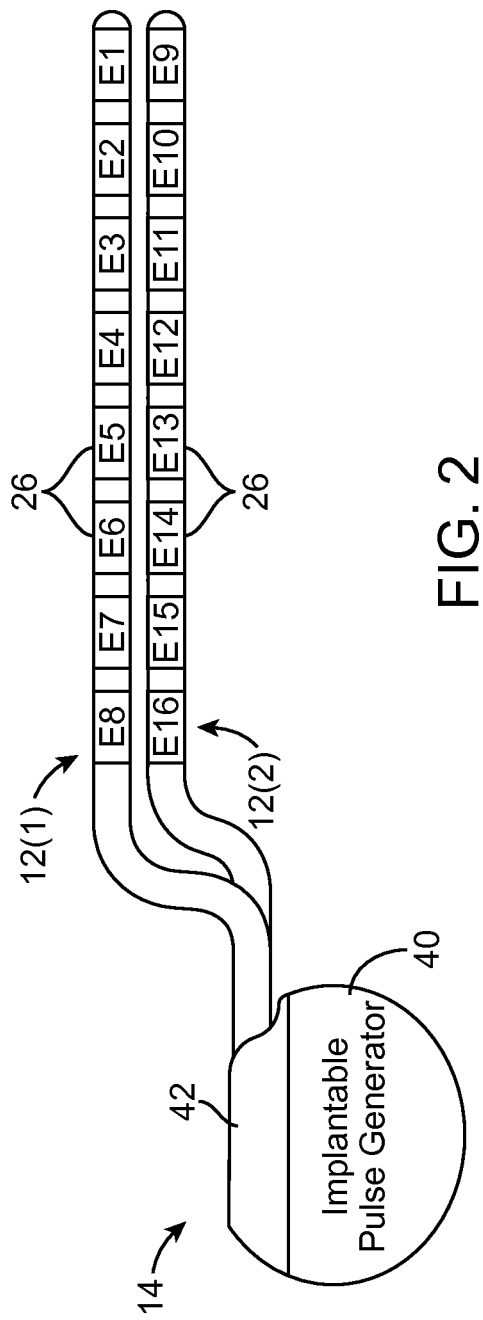
FIG. 2 is a plan view of an implantable pulse generator (IPG) and stimulation leads used in the SCS system of FIG. 1.

Referring now to FIG. 2, the external features of the neurostimulation leads 12 and the IPG 14 will be briefly described. Each of the neurostimulation leads 12 has eight electrodes 26 (respectively labeled E1-E8 for the lead 12(1) and E9-E16 for the lead 12(2)). The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

The IPG 14 comprises an outer case 40 for housing the electronic and other components (described in further detail below). The outer case 40 is composed of an electrically conductive, biocompatible material, such as titanium, and forms a hermetically sealed compartment wherein the internal electronics are protected from the body tissue and fluids. In some cases, the outer case 40 may serve as an electrode. The IPG 14 further comprises a connector 42 to which the proximal ends of the neurostimulation leads 12 mate in a manner that electrically couples the electrodes 26 to the internal electronics (described in further detail below) within the outer case 40. To this end, the connector 42 includes two ports (not shown) for receiving the proximal ends of the three percutaneous leads 12. In the case where the lead extensions 24 are used, the ports may instead receive the proximal ends of such lead extensions 24.

As will be described in further detail below, the IPG 14 includes pulse generation circuitry that provides electrical stimulation energy to the electrodes 26 in accordance with a set of parameters. Such parameters may comprise electrode combinations, which define the electrodes that are activated as anodes (positive), cathodes (negative), and turned off (zero), and electrical pulse parameters, which define the pulse amplitude (measured in milliamps or volts depending on whether the IPG 14 supplies constant current or constant voltage to the electrodes), pulse duration (measured in microseconds), pulse rate (measured in pulses per second), and pulse shape.

With respect to the pulse patterns provided during operation of the SCS system 10, electrodes that are selected to transmit or receive electrical energy are referred to herein as "activated," while electrodes that are not selected to transmit or receive electrical energy are referred to herein as "non-activated." Electrical energy delivery will occur between two (or more) electrodes, one of which may be the IPG case 40, so that the electrical current has a path from the energy source contained within the IPG case 40 to the tissue and a sink path from the tissue to the energy source contained within the case. Electrical energy may be transmitted to the tissue in a monopolar or multipolar (e.g., bipolar, tripolar, etc.) fashion.

Monopolar delivery occurs when a selected one or more of the lead electrodes 26 is activated along with the case 40 of the IPG 14, so that electrical energy is transmitted between the selected electrode 26 and case 40. Monopolar delivery may also occur when one or more of the lead electrodes 26 are activated along with a large group of lead electrodes located remotely from the one or more lead electrodes 26 so as to create a monopolar effect; that is, electrical energy is conveyed from the one or more lead electrodes 26 in a relatively isotropic manner. Bipolar delivery occurs when two of the lead electrodes 26 are activated as anode and cathode, so that electrical energy is transmitted between the selected electrodes 26. Tripolar delivery occurs when three of the lead electrodes 26 are activated, two as anodes and the remaining one as a cathode, or two as cathodes and the remaining one as an anode.

Figure 3:
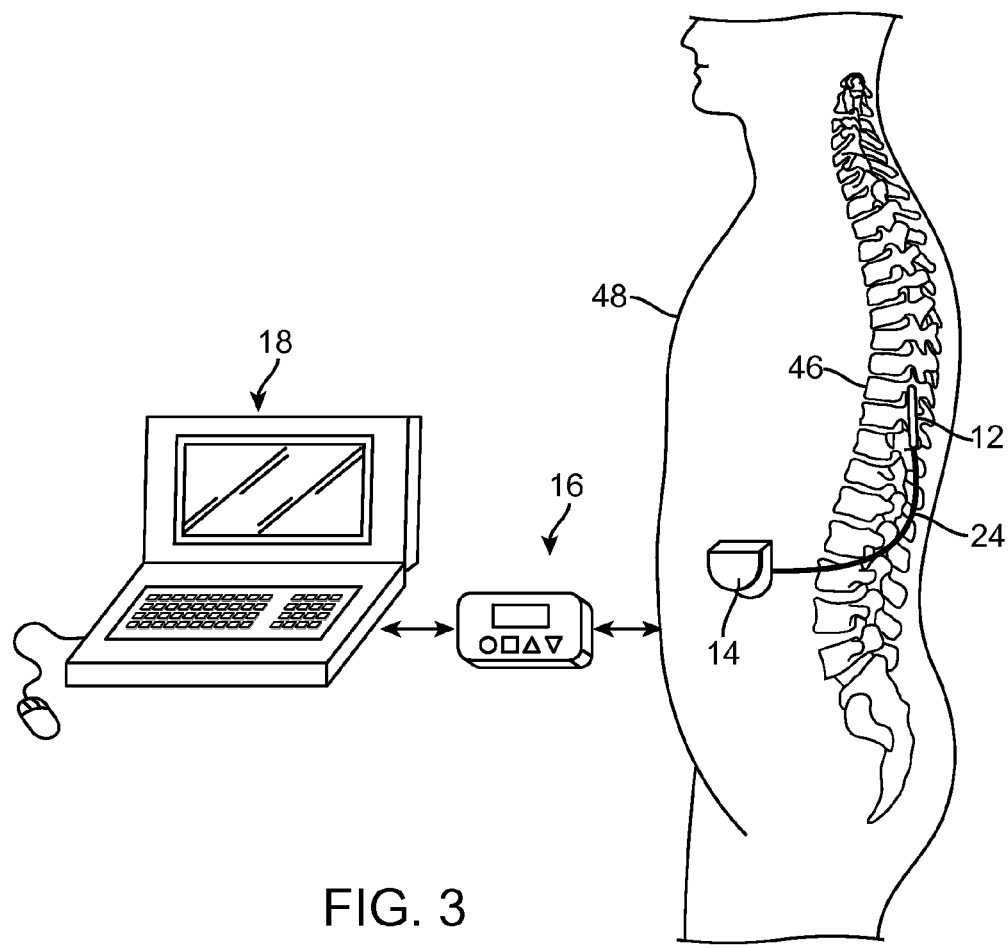
FIG. 3 is a plan view of the SCS system of FIG. 1 in use with a patient.

Referring to FIG. 3, the neurostimulation leads 12 are implanted within the spinal column 46 of a patient 48. The preferred placement of the neurostimulation leads 12 is adjacent, i.e., resting near, or upon the dura, adjacent to the spinal cord area to be stimulated. Due to the lack of space near the location where the neurostimulation leads 12 exit the spinal column 46, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the neurostimulation leads 12. As there shown, the CP 18 communicates with the IPG 14 via the RC 16. While the neurostimulation leads 12 are illustrated as being implanted near the spinal cord area of a patient, the neurostimulation leads 12 may be implanted anywhere in the patient's body, including a peripheral region, such as a limb, or the brain. After implantation, the IPG 14 is used to provide the therapeutic stimulation under control of the patient.

Figure 4:
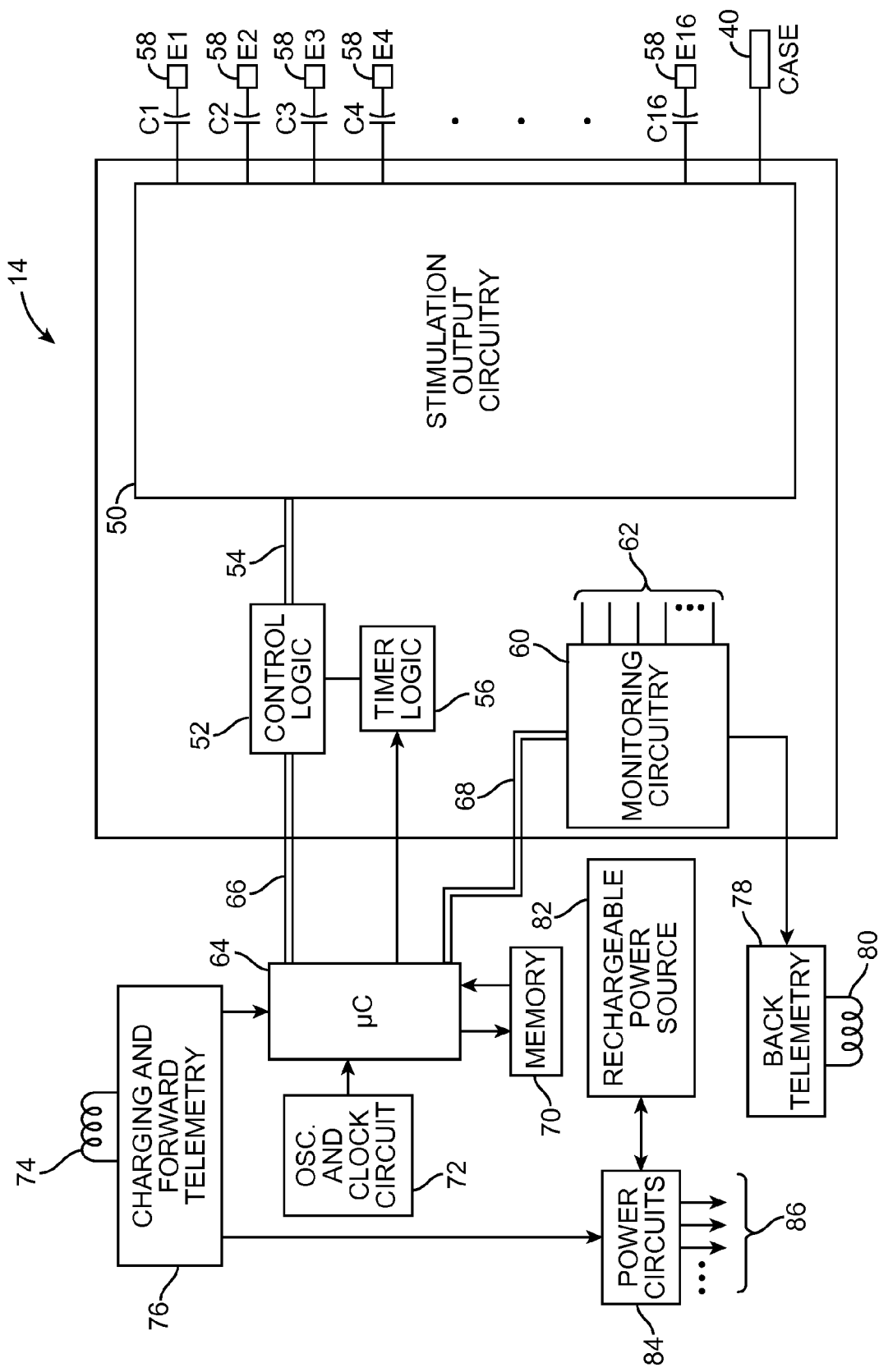
FIG. 4 is a block diagram of the internal components of the IPG of FIG. 1.

Turning next to FIG. 4, the main internal components of the IPG 14 will now be described. The IPG 14 includes stimulation output circuitry 50 configured for generating electrical stimulation energy in accordance with a defined pulsed waveform having a specified pulse amplitude, pulse rate, pulse width, pulse shape, and burst rate under control of control logic 52 over data bus 54. Control of the pulse rate and pulse width of the electrical waveform is facilitated by timer logic circuitry 56, which may have a suitable resolution, e.g., 10 µs. The stimulation energy generated by the stimulation output circuitry 50 is output via capacitors C1-C16 to electrical terminals 58 corresponding to the electrodes 26.

The stimulation output circuitry 50 may either comprise independently controlled current sources for providing stimulation pulses of a specified and known amperage to or from the electrodes 26, or independently controlled voltage sources for providing stimulation pulses of a specified and known voltage at the electrodes 26. The operation of this stimulation output circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The IPG 14 also comprises monitoring circuitry 60 for monitoring the status of various nodes or other points 62 throughout the IPG 14, e.g., power supply voltages, temperature, battery voltage, and the like. Notably, the electrodes 26 fit snugly within the tissue of the patient, and because the tissue is conductive, electrical parameter measurements can be taken at the electrodes 26. In addition to monitoring electrical parameter data on the lead electrodes 26, the monitoring circuitry 60 may also detect the presence of a large magnetic field (e.g., using a reed switch and/or a Hall-effect sensor) or a radio frequency (RF) noise characteristic of an MRI procedure.

Electrical signals can be transmitted between electrodes carried by one of the stimulation lead 12 and one or more other electrodes (e.g., electrodes on the same stimulation lead 12, electrodes on the other stimulation lead 12, the case 40 of the IPG 12, or an electrode affixed to the tissue), and then electrical parameter data can be measured in response to the transmission of the electrical signals.

Electrical parameter data can be measured using any one of a variety means. For example, the electrical parameter measurements can be made on a sampled basis during a portion of the time while the electrical stimulus pulse is being applied to the tissue, or immediately subsequent to stimulation, as described in U.S. patent application Ser. No. 10/364,436, which has previously been incorporated herein by reference. Alternatively, the electrical parameter measurements can be made independently of the electrical stimulation pulses, such as described in U.S. Pat. Nos. 6,516,227 and 6,993,384, which are expressly incorporated herein by reference. For example, electrical data measurements can be made in response to alternating current (AC) or pulsatile electrical signals, which preferably use amplitudes and pulsewidths (e.g., 1 mA for 20 µs) that generate no physiological response for the patient (i.e., subthreshold), but can alternatively be performed in response to stimulation pulses.

In the illustrated embodiment, electrical measurements are taken by the monitoring circuitry 60 for the purpose determining an electrode-tissue coupling efficiency and generating a coupling efficiency map for all of the lead electrodes 26. In particular, because implanted electrical stimulation systems depend upon the stability of the devices to be able to convey electrical stimulation pulses of known energy to the target tissue to be excited, the coupling efficiency between each of the lead electrodes 26 and the tissue may need to be measured.

For example, if the electrode impedance is too high, the respective electrode 26 may be inefficiently coupled to the tissue that it is to stimulate. As a result, an excessive amount of compliance voltage may need to be generated in order to effectively supply stimulation current to the electrode 26 if the stimulation output circuitry 50 uses current-controlled sources, thereby resulting in an inefficient use of the battery power, or the stimulation energy supplied to the electrode 26 may be otherwise inadequate if the stimulation output circuitry 50 uses voltage-controlled sources. Other electrical parameter data, such as field potential and evoked action potential, may also be measured to determine the coupling efficiency between the electrodes 26 and the tissue.

In the illustrated embodiment, electrical measurements may also be taken by the monitoring circuitry 60 for the purpose of determining whether there is a defect in one of the electrodes (e.g., an open circuit or a short circuit). For example, if the impedance is too high, that suggests the connector 42 and/or leads 12 may be open or broken.

Monopolar impedance measurements can be used to detect an open or broken circuit for each of the lead electrodes 26. If the impedance is too low, that suggests that there may be a short circuit somewhere in the connector 42 and/or leads 12. Bipolar impedance measurements can be used to detect short circuits between two lead electrodes 26. Thus, the monitoring circuitry 60 may assess and manage the integrity of the lead electrodes 26.

The impedance measurement technique may be performed by measuring impedance vectors, which can be defined as impedance values measured between selected pairs of electrodes (including the case electrode). The interelectrode impedance may be determined in various ways. For example, a known current can be applied between a pair of electrodes, a voltage between the electrodes can be measured, and an impedance between the electrodes can be calculated as a ratio of the measured voltage to known current. Or a known voltage can be applied between a pair of electrodes, a current between the electrodes can be measured, and an impedance between the electrodes can be calculated as a ratio of the known voltage to measured current.

Although in the illustrated embodiment, the electrical parameter data comprises electrical impedances, other suitable measurements, such as, e.g., electrical field potentials, can be obtained.

Field potentials can be especially valuable as they can provide more information as to whether an electrode is truly open- or short-circuited when impedance measurements are not always definitive. The combination of impedance and field potential measurements can be used to assess the electrode condition and detect potential open connection and/or insulation break.

The field potential measurement technique may be performed by generating an electrical field at selected ones of the lead electrodes 26 using constant current and recording the electrical field at other selected ones of the lead electrodes 26. This may be accomplished in one of a variety of manners. For example, an electrical field may be generated by conveying electrical energy to a selected one of the electrodes 26 and returning the electrical energy at the IPG case 40. Alternatively, multipolar configurations (e.g., bipolar or tripolar) may be created between the lead electrodes 26. Or, an electrode that is sutured (or otherwise permanently or temporarily attached, e.g., an adhesive or gel-based electrode) anywhere on the patient's body may be used in place of the case IPG outer case or lead electrodes 26. In either case, while a selected one of the electrodes 26 is activated to generate the electrical field, a selected one of the electrodes 26 (which may include the activated electrode or another electrode) is operated to record the voltage potential of the electrical field. Alternatively, a differential field potential measurement between a pair of electrodes that are different from the electrodes that source and return the energy can be taken.

Further details discussing the measurement of electrical parameter data, such as electrode impedance and field potential are set forth in U.S. patent application Ser. No. 10/364,436, entitled "Neural Stimulation System Providing Auto Adjustment of Stimulus Output as a Function of Sensed Impedance," U.S. patent application Ser. No. 10/364,434, entitled "Neural Stimulation System Providing Auto Adjustment of Stimulus Output as a Function of Sensed Pressure Changes," U.S. Pat. No. 6,993,384, entitled "Apparatus and Method for Determining the Relative Position and Orientation of Stimulation Leads," and U.S. patent application Ser. No. 11/096,483, entitled "Apparatus and Methods for Detecting Migration of Stimulation Leads," which are expressly incorporated herein by reference.

The IPG 14 further comprises processing circuitry in the form of a microcontroller (μC) 64 that controls the control logic 52 over data bus 66, and obtains status data from the monitoring circuitry 60 via data bus 68. The IPG 14 additionally controls the timer logic 56. The IPG 14 further comprises memory 70 and oscillator and clock circuit 72 coupled to the microcontroller 64. The microcontroller 64, in combination with the memory 70 and oscillator and clock circuit 72, thus comprise a microprocessor system that carries out a program function in accordance with a suitable program stored in the memory 70. Alternatively, for some applications, the function provided by the microprocessor system may be carried out by a suitable state machine.

Thus, the microcontroller 64 generates the necessary control and status signals, which allow the microcontroller 64 to control the operation of the IPG 14 in accordance with a selected operating program and stimulation parameters. In controlling the operation of the IPG 14, the microcontroller 64 is able to individually generate stimulus pulses at the electrodes 26 using the stimulation output circuitry 50, in combination with the control logic 52 and timer logic 56, thereby allowing each electrode 26 to be paired or grouped with other electrodes 26, including the monopolar case electrode, to control the polarity, amplitude, rate, pulse width and channel through which the current stimulus pulses are provided.

Significantly, in response to an external signal initiated by a user from the RC 16 and/or CP 18 or otherwise initiated by the sensing of a magnetic and/or RF field characteristic of an MRI by the monitoring circuitry 60, the microcontroller 64 switches the SCS system 10 from a normal-mode, during which the monitoring circuitry 60 takes each electrical parameter measurement at the lead electrodes 26 only when prompted by the user via the RC 16 and/or CP 18, and an MRI mode, during which the monitoring circuitry 60 repeatedly takes electrical parameter measurements at the lead electrodes 26 without user interaction until the IPG 14 is switched back to the normal-mode.

Based on the repeated electrical parameter measurements when the IPG 14 is in the MRI mode, corrective actions may be taken by the IPG 14, or as described in further detail below, the RC 16. In particular, the microcontroller 64 processes the electrical parameter measurements to determine whether a corrective action should be taken.

For example, the microcontroller 64 may determine that one of the lead electrodes 26 is faulty in that it has an open circuit or a short circuit. In this case, the microcontroller 64 may perform a corrective action by alerting the user. To this end, the IPG 14 may include a mechanical transducer (not shown) that outputs an alert signal in form of a vibratory signal (e.g., the case 100 can vibrate). Alternatively, the outputted alert signal can take the form of a modulated neurostimulation signal (e.g., pulsing a neurostimulation signal on and off at a frequency less than the pulse frequency (e.g., every three seconds) or repeatedly increasing and decreasing the amplitude of the neurostimulation signal) that can be perceived by the patient as distinguished from normal, operative stimulation used for the therapy.

As another example, the microcontroller 64 may determine that the coupling efficiency between one of the electrodes and the tissue has significantly changed by determining an electrode-tissue coupling efficiency at each of the lead electrodes 26 and comparing each of these determined electrode-tissue coupling efficiencies to a reference electrode-tissue coupling efficiency for the lead electrode 26 previously stored in the memory 70. If the comparison reveals a significant change in the electrode-tissue coupling efficiency for any particular lead electrode 26, the microcontroller 64 may generate a new set of stimulation parameters by adjusting at least one stimulation parameter in accordance with which the stimulation output circuitry 50 generates and outputs the electrical stimulation energy. For example, if the coupling efficiency associated with an active electrode has decreased, the microcontroller 64 may increase the amplitude of the electrical stimulation energy delivered to that electrode. In contrast, if the coupling efficiency associated with an active electrode has increased, the microcontroller 64 may decrease the amplitude of the electrical stimulation energy delivered to that electrode.

Because the microcontroller 64 processes the electrical parameter measurements and performs the necessary corrective actions, the IPG 14 may not need to establish connection with the RC 16 after the SCS system 10 has been placed in the MRI mode. Alternatively, the electrical parameter measurements can be conveyed to the RC 16, in which case, the electrical parameter measurements may be processed by the RC 16, and the IPG 14 may perform the corrective actions in response to an instruction transmitted back to the IPG 14 from the RC 16.

When in the MRI mode, precautions may also be taken to prevent the large magnetic fields generated by the MRI from damaging the IPG 14 or inadvertently stimulating the patient, as discussed in U.S. Provisional Patent Application Ser. 61/612,241, entitled "Neurostimulation System for Preventing Magnetically Induced Currents in Electronic Circuitry," and/or the IPG 14 may be prevented from shutting down in order to monitor the magnetic fields generated by the MRI, as discussed in U.S. Provisional Patent Application Ser. No. 61/664,061, entitled "Neurostimulation System for Enabling Magnetic Field Sensing with a Shut-Down Hall Sensor, which are expressly incorporated herein by reference.

The IPG 14 further comprises an alternating current (AC) receiving coil 74 for receiving programming data (e.g., the operating program, and/or stimulation parameters, and/or a signal for placing the IPG 14 in either the normal-mode or the MRI mode) from the RC 16 and/or CP 18 in an appropriate modulated carrier signal, and charging and forward telemetry circuitry 76 for demodulating the carrier signal it receives through the AC receiving coil 74 to recover the programming data, which programming data is then stored within the memory 70, or within other memory elements (not shown) distributed throughout the IPG 14.

The IPG 14 further comprises back telemetry circuitry 78 and an alternating current (AC) transmission coil 80 for sending informational data sensed through the monitoring circuitry 60 to the RC 16 and/or CP 18. The back telemetry features of the IPG 14 also allow its status to be checked. For example, when the RC 16 and/or CP 18 initiates a programming session with the IPG 14, the capacity of the battery is telemetered, so that the RC 16 and/or CP 18 can calculate the estimated time to recharge. Any changes made to the current stimulus parameters are confirmed through back telemetry, thereby assuring that such changes have been correctly received and implemented within the implant system. Moreover, upon interrogation by the RC 16 and/or CP 18, all programmable settings stored within the IPG 14 may be uploaded to the RC 16 and/or CP 18. If the RC 16 is to perform the corrective action when the SCS system 10 is in the MRI mode, the back telemetry features of the IPG 14 may also be used to instruct the RC 16 to perform such corrective features after processing the acquired electrical parameter measurements by the IPG 14.

The IPG 14 further comprises a rechargeable power source 82 and power circuits 84 for providing the operating power to the IPG 14. The rechargeable power source 82 may, e.g., comprise a lithium-ion or lithium-ion polymer battery. The rechargeable battery 82 provides an unregulated voltage to the power circuits 84. The power circuits 84, in turn, generate the various voltages 86, some of which are regulated and some of which are not, as needed by the various circuits located within the IPG 14. The rechargeable power source 82 is recharged using rectified AC power (or DC power converted from AC power through other means, e.g., efficient AC-to-DC converter circuits, also known as "inverter circuits") received by the AC receiving coil 74. To recharge the power source 82, an external charger (not shown), which generates the AC magnetic field, is placed against, or otherwise adjacent, to the patient's skin over the implanted IPG 14. The AC magnetic field emitted by the external charger induces AC currents in the AC receiving coil 74. The charging and forward telemetry circuitry 76 rectifies the AC current to produce DC current, which is used to charge the power source 82. While the AC receiving coil 74 is described as being used for both wirelessly receiving communications (e.g., programming and control data) and charging energy from the external device, it should be appreciated that the AC receiving coil 74 can be arranged as a dedicated charging coil, while another coil, such as coil 80, can be used for bi-directional telemetry.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the system 10 may alternatively utilize an implantable receiver-stimulator (not shown) connected to leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 5:
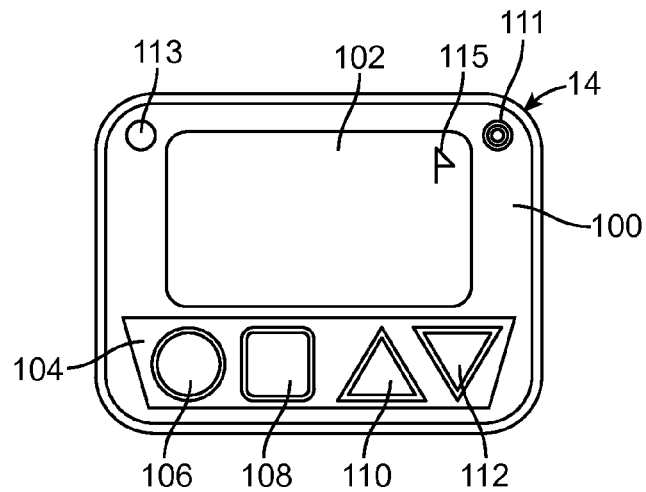
FIG. 5 is front view of a remote control (RC) used in the SCS system of FIG. 1.

Referring now to FIG. 5, one exemplary embodiment of an RC 16 will now be described. As previously discussed, the RC 16 is capable of communicating with the IPG 14, CP 18, or ETS 20. The RC 16 comprises a casing 100, which houses internal componentry (including a printed circuit board (PCB)), and a lighted display screen 102 and button pad 104 carried by the exterior of the casing 100. In the illustrated embodiment, the display screen 102 is a lighted flat panel display screen, and the button pad 104 comprises a membrane switch with metal domes positioned over a flex circuit, and a keypad connector connected directly to a PCB. In an optional embodiment, the display screen 102 has touchscreen capabilities. The button pad 104 includes a multitude of buttons 106, 108, 110, and 112, which allow the IPG 14 to be turned ON and OFF, provide for the adjustment or setting of stimulation parameters within the IPG 14, and provide for selection between screens.

In the illustrated embodiment, the button 106 serves as an ON/OFF button that can be actuated to turn the IPG 14 ON and OFF. The button 108 serves as a select button that allows the RC 106 to switch between screen displays and/or parameters. The buttons 110 and 112 serve as up/down buttons that can be actuated to increase or decrease any of stimulation parameters of the pulse generated by the IPG 14, including pulse amplitude, pulse width, and pulse rate. The button pad 104 can be actuated to conventionally obtain and display electrode impedance measurements from the IPG 14 on demand, which may indicate electrode-tissue coupling efficiency or a faulty electrode. The button pad 104 can also be actuated to switch the IPG 14 between the normal-mode and the MRI mode via selection of menus.

Figure 6:
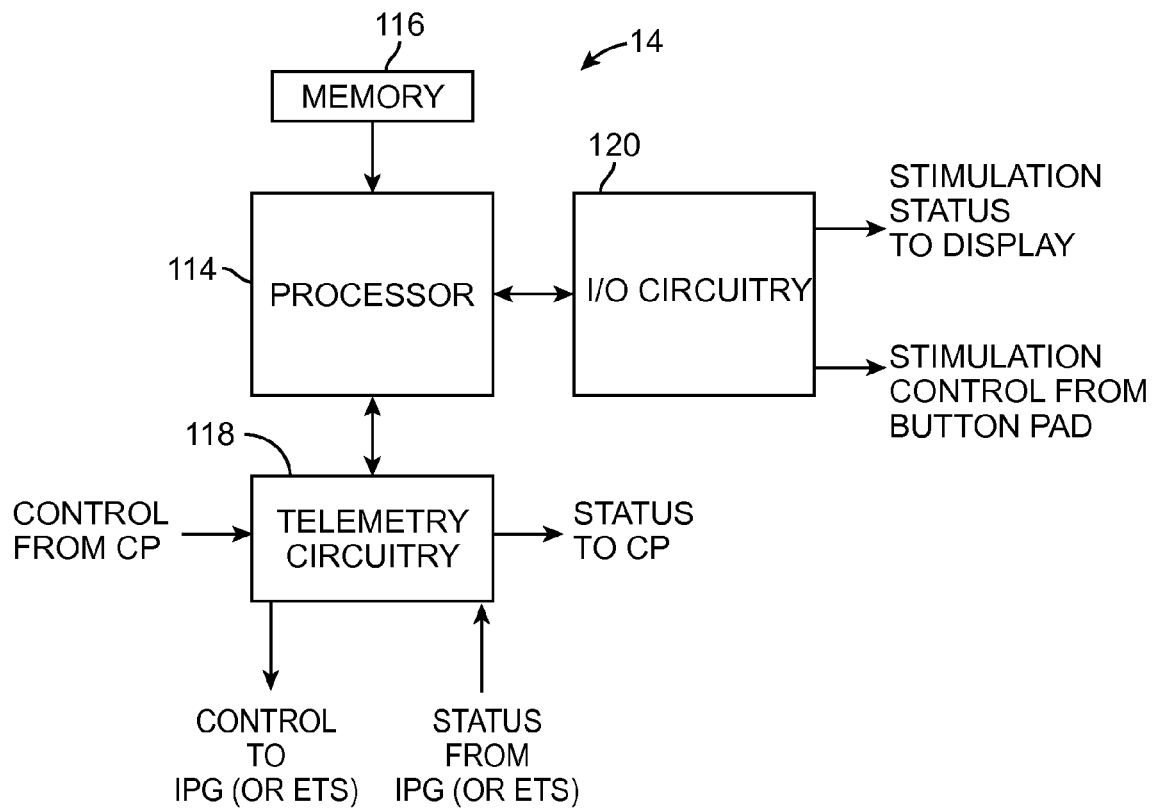
FIG. 6 is a block diagram of the internal components of the RC of FIG. 5.

Referring to FIG. 6, the internal components of an exemplary RC 16 will now be described. The RC 16 generally includes a controller/processor 114 (e.g., a microcontroller), memory 116 that stores an operating program for execution by the controller/processor 114, and telemetry circuitry 118 for transmitting control data (including stimulation parameters and requests to provide status information) to the IPG 14 and receiving control signals (e.g., a signal to take corrective action) and status information (including the electrical parameter measurements) from the IPG 14 via link 34 (shown in FIG. 1), as well as receiving the control data from the CP 18 and transmitting the status data to the CP 18 via link 36 (shown in FIG. 1). The RC 16 further includes input/output circuitry 120 for receiving stimulation control signals from the button pad 104 and transmitting status information to the display screen 102 (shown in FIG. 5).

Notably, while the controller/processor 114 is shown in FIG. 6 as a single device, the processing functions and controlling functions can be performed by a separate controller and processor. Thus, it can be appreciated that the controlling functions described below as being performed by the RC 16 can be performed by a controller, and the processing functions described below as being performed by the RC 16 can be performed by a processor. Further details of the functionality and internal componentry of the RC 16 are disclosed in U.S. Pat. No. 6,895,280, which has previously been incorporated herein by reference.

The RC 16 is capable of performing a corrective action based on the electrical parameter measurements repeatedly acquired by the IPG 14 when the SCS system 10 is in the MRI mode. This corrective action can be performed in addition to, or as an alternative to, the previously described corrective actions performed by the IPG 14.

In particular, in the case where processing of the electrical parameter measurements is performed in the IPG 14, as discussed above, a control signal may be received from the IPG 14 instructing the RC 16 to take a corrective action.

For example, in the case where the IPG 14 determines that one of the lead electrodes 26 is faulty in that it has an open circuit or a short circuit, the controller/processor 114 may perform a corrective action by alerting a user. To this end, the RC 16 includes a binary indicator in the form of an audio transducer 111 (i.e., a speaker) (shown in FIG. 5) that alerts the user with distinctive tones (e.g., with a series of beeps, music, or voice messages) when a faulty lead electrode 26 is detected by the IPG 14 in the MRI mode. Alternatively or optionally, the RC 16 may further include another binary indicator in the form of a visual indicator 113 (shown in FIG. 5) that flashes (or otherwise changes in some fashion) in order to alert the user when a faulty lead electrode 26 is detected by the IPG 14 in the MRI mode. Other types of indicators can be used to alert the user to a faulty lead electrode 26. For example, the RC 16 may include a mechanical transducer that vibrates when a faulty lead electrode 26 is detected. As another example, a binary indicator 115 can be displayed on the display screen 102 (shown in FIG. 5) to indicate two different conditions. For example, a green flag may be displayed to indicate no or low risk electrode conditions, and a red flag may be displayed to indicate a high risk electrode condition.

As another example, in the case where the IPG 14 determines that the coupling efficiency between one of the electrodes and the tissue has changed, the controller/processor 114 may generate a new set of stimulation parameters by adjusting at least one stimulation parameter in accordance with which the stimulation output circuitry 50 generates and outputs the electrical stimulation energy. This new set of stimulation parameters can be transmitted from the RC 16 to reprogram the IPG 14.

In the case where processing of the electrical parameter measurements is not performed in the IPG 14, the electrical parameter measurements will be transmitted from the IPG 14, in which case, the controller/processor 114 will process the electrical parameter measurements and take the corrective action(s) described above.

Figure 7:
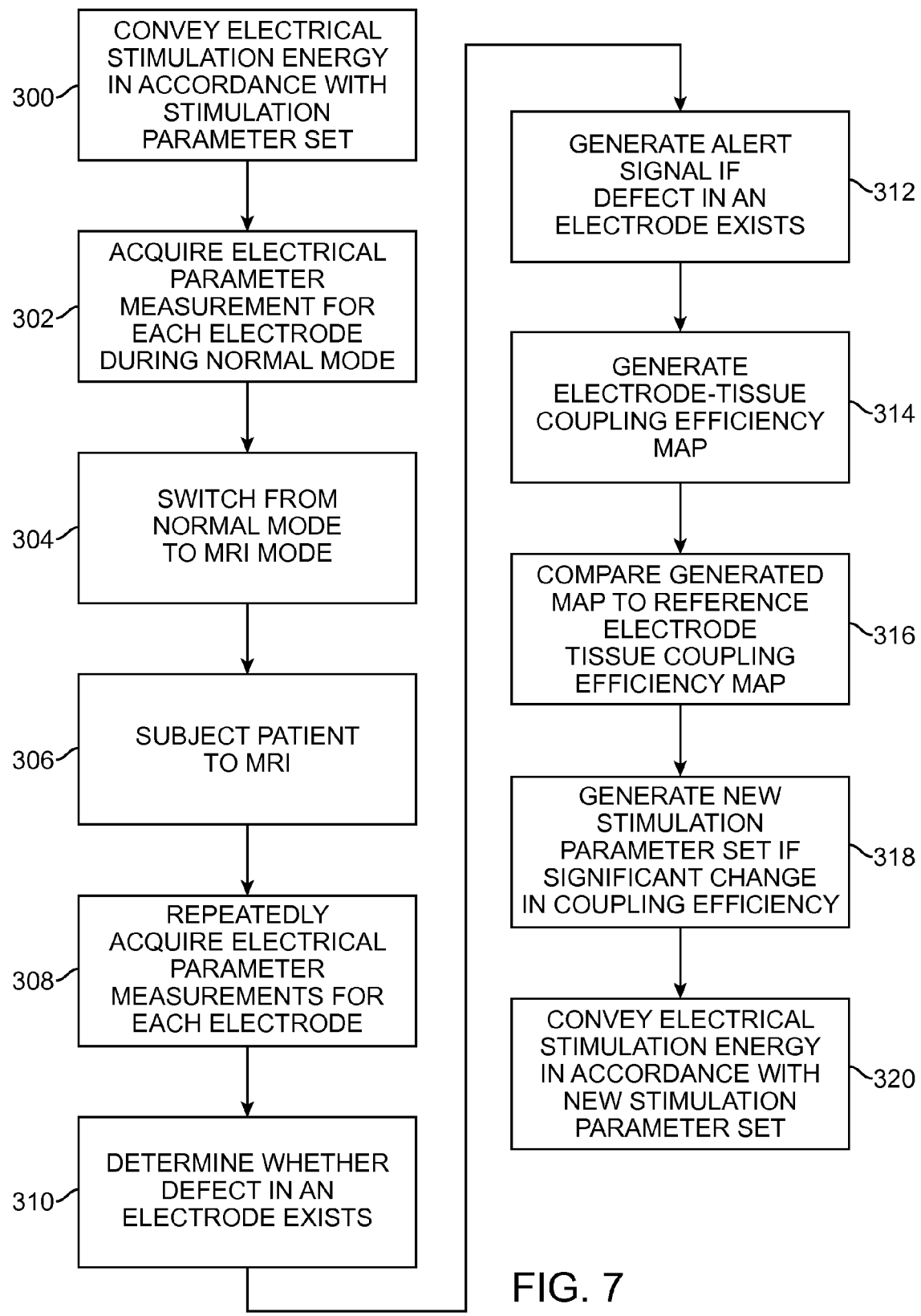
FIG. 7 is a flow diagram illustrating a technique used to operate the SCS system of FIG. 1 in an MRI mode.

Having described the structure and function of the SCS system 10, one technique for operating the system 10 in an MRI mode will now be described with reference to FIG. 7.

While the IPG 14 is currently in the normal mode, electrical stimulation energy may be conveyed from the IPG 14 to the lead electrodes 26 in accordance with a stimulation parameter set (step 300). Notably, although it may be a rare occurrence when it is necessary or desirable to convey electrical stimulation energy in the context of SCS during an MRI, in other neurostimulation contexts, such as pacing a heart, it is desirable, if not necessary, to continue the stimulation regimen. Prior to the performance of an MRI on the patient implanted with the IPG 14, the RC 16 is operated to obtain an impedance measurement at each of the lead electrodes 26 from the IPG 14 (step 302). This can be performed to ensure that the lead electrodes 26 are not defective prior to initiation of the MRI and/or to provide a reference electrode-tissue coupling efficiency map to which subsequent coupling efficiency maps can be compared.

The IPG 14 may then be switched to the MRI mode by transmitting a programming signal from the RC 16 to the IPG 14 (step 304). At any time when the IPG 14 is in the MRI mode, the patient may undergo an MRI (step 306). In response to switching the IPG 14 to the MRI mode, the IPG 14 repeatedly acquires electrical parameter measurements at each of the lead electrodes 26 from the IPG 14 (step 308). Next, the IPG 14, or optionally the RC 16, determines whether there is a defect in any of the lead electrodes 26 based on the acquired electrical parameter measurements (step 310). If a defect in any of the lead electrodes 26 is determined to exist, an alert signal is generated (step 312). In any event, the IPG 14, or optionally the RC 16, generates an electrode-tissue coupling efficiency map for the lead electrodes 26 (step 314), compares it to a reference electrode-tissue coupling efficiency map acquired previous to the MRI (step 316), and if the comparison reveals that a significant change in the electrode-tissue coupling has occurred during the MRI, the IPG 14 and/or RC 16 generates a new set of stimulation parameters based on the comparison (step 318). The electrical stimulation energy may then be conveyed from the IPG 14 to the lead electrodes 26 in accordance with the new stimulation parameter set (step 320). In the particular condition of therapy administered during an MRI, the new stimulation parameter set includes a "complete disconnect" condition, in which the faulty electrode(s) are disconnected from the stimulation circuitry and any electrical access to the IPG case, as well as all electrodes being disconnected from the stimulation circuitry and any electrical access to the IPG case. The IPG 14 may optionally be switched to the normal mode by transmitting a programming signal from the RC 16 to the IPG 14, after which another electrode-tissue coupling efficiency map may be generated.

Although the foregoing techniques have been described as being at least partially implemented in the RC 16, it should be noted that these techniques may be at least, in part, be alternatively or additionally implemented in the CP 18. Furthermore, although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A neurostimulation system, comprising:
    at least one stimulation lead carrying at least one electrode;
    stimulation output circuitry coupled to the at least one stimulation lead, the stimulation output circuitry configured for outputting electrical stimulation energy to the at least one electrode in accordance with a set of stimulation parameters;
    a controller/processor configured for placing the stimulation system between a Magnetic Resonance Imaging (MRI) operating mode and a normal operating mode; and
    monitoring circuitry configured for acquiring electrical parameter measurements at each of the at least one electrode in response to the placement of the stimulation system in the MRI mode;
    wherein the controller/processor is further configured for determining an electrode-tissue coupling efficiency based on at least one of the repeatedly acquired electrical parameter measurements, comparing the determined electrode-tissue coupling efficiency to a reference electrode-tissue coupling efficiency, and generating a new set of stimulation parameters based on the comparison, wherein the stimulation output circuitry is configured for outputting electrical stimulation energy to the at least one electrode in accordance with the new set of stimulation parameters.

2. The neurostimulation system of claim 1, wherein each of the electrical parameter measurements comprises one of an impedance measurement and a field potential measurement.

3. The neurostimulation system of claim 1, wherein the controller/processor is configured for instructing the stimulation output circuitry to convey electrical energy to each of the at least one electrode, wherein each of the electrical parameter measurements is taken by measuring at least one electrical parameter in response to the conveyed electrical energy.

4. The neurostimulation system of claim 1, wherein the controller/processor is further configured for determining a defect in at least one of the electrodes based on the at least one of the acquired electrical parameter measurements, and generating an alert signal in response to determining the defect.

5. The neurostimulation system of claim 4, wherein the defect is one of a short circuit and an open circuit.

6. The neurostimulation system of claim 4, wherein the alert signal is a binary signal.

7. The neurostimulation system of claim 4, wherein the alert signal is one of a visual signal, an aural signal, a vibratory signal, and a modulated neurostimulation signal.

8. The neurostimulation system of claim 1, further comprising a user interface configured for receiving input from a user, wherein the controller/processor is configured for placing the stimulation system in the MRI operating mode in response to the user input.

9. The neurostimulation system of claim 1, wherein the monitoring circuitry is configured for sensing energy emitted by an MRI scanner, and the controller/processor is configured for placing the stimulation system in the MRI operating mode in response to the sensed energy.

10. A method of operating an implantable neurostimulation device configured for outputting electrical stimulation energy to at least one electrode in accordance with a set of stimulation parameters, the method comprising:
    switching the implantable neurostimulation device from a normal operating mode to a Magnetic Resonance Imaging (MRI) operating mode;
    acquiring electrical parameter measurements at each of the at least one electrode in response to the placement of the implantable stimulation system in the MRI mode;
    determining an electrode-tissue coupling efficiency based on at least one of the repeatedly acquired electrical parameter measurements, comparing the determined electrode-tissue coupling efficiency to a reference electrode-tissue coupling efficiency, generating a new set of stimulation parameters based on the comparison, and outputting electrical stimulation energy to the at least one electrode in accordance with the new set of stimulation parameters.

11. The method of claim 10, wherein each of the electrical parameter measurements comprises one of an impedance measurement and a field potential measurement.

12. The method of claim 10, further comprising conveying electrical energy to each of the at least one electrode, wherein each of the electrical parameter measurements is taken by measuring at least one electrical parameter in response to the conveyed electrical energy.

13. The method of claim 10, further comprising determining a defect in at least one of the electrodes based on the at least one of the acquired electrical parameter measurements, and generating an alert signal in response to determining the defect.

14. The method of claim 13, wherein the defect is one of a short circuit and an open circuit.

15. The method of claim 13, wherein the alert signal is a binary signal.

16. The method of claim 13, wherein the alert signal is one of a visual signal, an aural signal, a vibratory signal, and a modulated neurostimulation signal.

17. The method of claim 10, further comprising receiving input from a user, wherein the implantable neurostimulation device is switched to the MRI operating mode in response to the user input.

18. The method of claim 10, further comprising sensing energy emitted by an MRI scanner, wherein the implantable neurostimulation device is switched to the MRI operating mode in response to the sensed energy.

* * * * *